United States Patent [19]

Coyle et al.

[11] Patent Number: 4,912,218

[45] Date of Patent: Mar. 27, 1990

[54] SUBSTITUTED TRIAZINE DERIVATIVES

[75] Inventors: John D. Coyle, Buckinghamshire; Averil M. Horton, Richmond, both of United Kingdom

[73] Assignee: Cookson Group PLC, London, United Kingdom

[21] Appl. No.: 117,798

[22] Filed: Nov. 5, 1987

[30] Foreign Application Priority Data

Nov. 12, 1986 [GB] United Kingdom ............... 8627059

[51] Int. Cl.$^4$ ........................................ C07D 251/24
[52] U.S. Cl. ..................................................... 544/216
[58] Field of Search ........................................ 544/216

[56] References Cited

U.S. PATENT DOCUMENTS 3,264,293 8/1966 Heimberger ..................... 544/216
4,330,590 5/1982 Vesley ................................ 544/216
4,391,687 7/1983 Vesley ................................ 544/216

FOREIGN PATENT DOCUMENTS 60-60104 4/1985 Japan .

OTHER PUBLICATIONS

Wakabayashi et al., Bull. Chem. Soc. Japan, 1969, 42, pp. 2924 to 2930.
Schmelzer et al., Angew., Chem., 1966, 72, p. 982 et seq.
Schaefer et al., J. Org. Chem., 1964, 29, p. 1527 et seq.

Primary Examiner—John M. Ford
Attorney, Agent, or Firm—Kenyon & Kenyon

[57] ABSTRACT

A triazine derivative of the formula

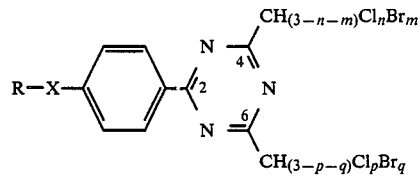

wherein R is an alkyl group or an aryl group,
X is S, Se or Te,
n or m is 0, or each is an integer of from 1 to 3, the total sum of n+m not being greater than 3, and p or q is 0, or each is an integer of from 1 to 3, the total sum of p+q not being greater than 3. The triazines may be used in photopolymerizable compositions.

9 Claims, No Drawings

SUBSTITUTED TRIAZINE DERIVATIVES

The present invention relates to substituted triazine derivatives and, in particular, to substituted triazine derivatives which contain a chalcogenide substituent.

2-Substituted-4,6-bis(trihalomethyl)-1,3,5-triazines have been used to initiate photopolymerisation in photosensitive resin compositions (e.g. JP60/60104, 6th Apr., 1985, Fuji Photo Film Co. Ltd) and to generate strong colour changes on exposure of positive-acting compositions (e.g. US 4350753, 21st Sept., 1982, Polychrome Corp.)

We have now developed certain substituted triazine derivatives which can initiate polymerization or generate strong colour changes. These compounds contain a 4-alkylthiophenyl, 4-arylthiophenyl group, or the selenium or tellurium analogues thereof, and absorb more strongly at the wavelengths commonly used in lithographic print down frames (exposure units) than do structurally similar triazines which do not contain the sulphur, selenium or tellurium linkages.

Accordingly, the present invention provides a triazine derivative of the general formula:

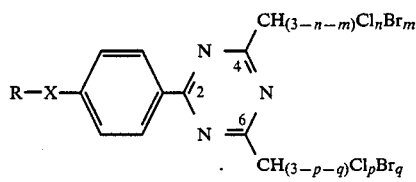

wherein R is an alkyl group or an aryl group,

X is S, Se or Te, n or m is 0, or each is an integer of from 1 to 3, the total sum of n+m not being greater than 3, and p or q is 0, or each is an integer of from 1 to 3, the total sum of p+q not being greater than 3.

Preferably, the compounds of the invention are compounds in which the substituents at positions 4 and 6 of the triazine group are identical. More preferably n is 3, m is 0, p is 3 and q is 0.

The group R is preferably an alkyl group containing from 1 to 20 carbon atoms, preferably 1 to 6 carbon atoms, most preferably a methyl or ethyl group, or a phenyl or substituted phenyl group.

A preferred compound of the present invention is 2-(4-methylthiophenyl)-4,6-bis(trichloromethyl)-1,3,5-triazine, which has the following formula:

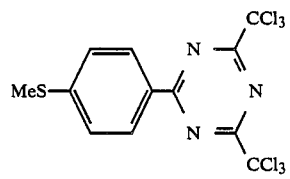

Other preferred compounds of the invention are 2-(4-ethylthiophenyl)-4,6-bis(trichloromethyl)-1,3,5-triazine, 2-(4-stearylthiophenyl)-4,6-bis(trichloromethyl)-1,3,5-triazine, 2-(4-phenylthiophenyl)-4,6-bis(trichloromethyl)-1,3,5-triazine, 2-(4-(4-methoxyphenyl)thiophenyl)-4,6-bis-trichloromethyl)-1,3,5-triazine and 2-(4-methylthiophenyl)-4,6-bis(tribromomethyl)-1,3,5-triazine.

The compounds of the present invention may be prepared by the general method described in Bull. Chem. Soc. Japan, 1969, 42, pages 2924 to 2930, by cotrimerization of the halogenated acetonitrile with a substituted benzonitrile, in the presence of hydrochloric acid and a Friedel-Crafts catalyst, e.g. AlCl₃, AlBr₃, TiCl₄, or boron trifluoride etherate. A typical reaction sequence is given below:

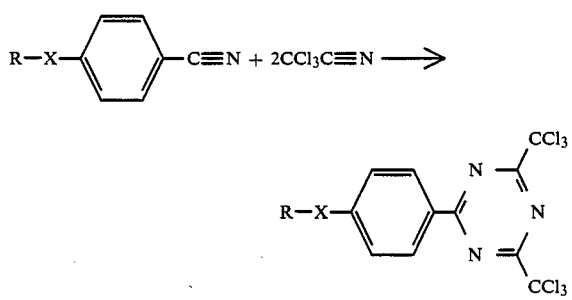

Other ways of synthesizing the compounds are by reacting aryl amidines with polychloroaza-alkenes according to the method published in Angew., Chem., 1966, 72, p. 982 et seq. Methods for the subsequent chlorination and bromination of alkyl substituents in s-triazines and exchange reaction in which bromine atoms in tribromomethyl groups may be replaced by hydrogen are disclosed in J. Org. Chem., 1964, 29, p. 1527 et. seq. Some of the nitriles used in the co-trimerization may be prepared by simple methods known in the art, for example by the dehydration of carboxylic acid amides or oximes, or by the reaction of aromatic bromine compounds with cuprous cyanide.

The compounds of the present invention are photoinitiators, i.e. initiate polymerization reactions, and/or are capable of causing colour changes in coloured systems.

For use as photoinitiators, the compounds of the present invention are effective in amounts of from about 0.05 to 20 percent by weight, with amounts in the range of up to 10 percent by weight and more preferably from 3 to 7 percent by weight being particularly preferred. The photoinitiators may be used, for example, to initiate photopolymerization reactions which are triggered by free radicals. Suitable monomers which can be photopolymerized are acrylates, methacrylates, vinyl esters and vinylamides. The polymerizable compositions may contain conventional additives, such as fillers, dyestuffs, plasticizers or polymerization inhibitors.

The compounds of the present invention are also capable of causing colour changes in coloured systems during photolysis or of initiating colour formation in colour couplers, e.g. leuco compounds. Colour changes are of particular importance in the manufacture of lithographic plates because they make it possible for the plates to be examined before they are developed. It is well known that depending upon the composition of the radiation-sensitive coating employed a lithographic printing plate may reproduce the image to which it is exposed, in which case it is termed a positive-working plate, or it may produce an image complementary to the one to which it is exposed, in which case it is termed a negative-working plate. The compounds of the present invention may be used in either positive-working or negative-working lithographic plates.

Accordingly, the present invention also includes within its scope a coating composition for a positive-working or a negative-working lithographic printing plate which comprises from 0.05 to 20 percent by weight of total solids of a novel substituted triazine of the invention. Preferably these compositions comprise up to 10 percent, more preferably from 1 to 7 percent by weight, and most preferably about 5 percent by weight of total solids of the novel substituted triazine.

The present invention will be further described with reference to the following Examples.

EXAMPLE 1

Synthesis of 2-(4-methylthiophenyl)-4,6-bis(trichlomethyl)-1,3,5-triazine 4-(Methylthio)benzonitrile (24.5 g), trichlorocetonitrile (47.8 g) and aluminium tribromide (0.48 g), were placed in a 3-necked flask, and the mixture was saturated with gaseous HCl whilst being maintained at a temperature of from $-10°$ to $0°$ C. for 3 hours. After standing for 2 days the mixture was heated and poured into water (2 liters); the precipitated solids were filtered and recrystallised from ethanol—yield 70%.

m.p. 149°–151° C.

I.R. (KBr) 695, 720, 770, 820, 845, 1020, 1090, 1190, 1340, 1400, 1510, 1550, 1595, 2925 cm$^{-1}$.

U.V. (EtOH) $\lambda_{max}$358 nm, $\epsilon_{max}$37,960 1 mol$^{-1}$cm$^{-1}$, $\lambda_{max}$235 nm, $\epsilon_{max}$12,300 1 mol$^{-1}$cm$^{-1}$.

N.M.R. (CDCl$_3$) $\delta$2.6(3H, s), 7.3(2H, d), 8.5(2H, d).

EXAMPLE 2

Synthesis of 2-(4-ethylthiophenyl)-4,6-bis(trichloromethyl)-1,3,5-triazine 4-(Ethylthio)benzonitrile (3.0 g), trichloroacetonitrile (8 g) and aluminium tribromide (0.1 g) were placed in a 3-necked flask and the mixture was saturated with gaseous HCl whilst being maintained at a temperature of from $-5°$ to $+5°$ C. for 30 minutes. After standing for 3 days, the mixture was heated and poured into methanol (500 ml); the precipitated solids were filtered and recrystallised from ethanol—yield 68%.

m.p. 112°–113° C.

I.R. (Nujol) 695, 770, 820, 845, 920, 990, 1010, 1090, 1110, 1140, 1190, 1345, 1395, 1505, 1550, 1595 cm$^{-1}$.

U.V. (EtOH) $\lambda_{max}$362 nm, $\epsilon_{max}$11,300 1 mol$^{-1}$cm$^{-1}$, $\lambda_{max}$237 nm, $\epsilon_{max}$ 3,950 1 mol$^{-1}$cm$^{-1}$.

N.M.R. (CDCl$_3$) $\delta$1.4(3H, t), 3.1(2H, q), 7.4(2H, d), 8.6(2H, d).

EXAMPLE 3

Synthesis of 2-(4-stearylthiophenyl)-4,6-bis-(trichloromethyl)-1,3,5-triazine 4-(Stearylthio)benzonitrile (10 g), trichloroacetonitrile (10 g) and aluminium tribromide (0.3 g) were placed in a 3-necked flask and the mixture saturated with gaseous HCl whilst being maintained at a temperature of 50° C. for 30 minutes. After standing for 3 days the mixture was heated and poured into methanol (1 liter); the precipitated solids were collected and recrystallised from ethanol—yield 49%.

m.p. 64°–66° C.

I.R. (Nujol) 670, 695, 715, 720, 770, 780, 820, 850, 920, 990, 1010, 1090, 1185, 1340, 1400, 1510, 1545, 1595 cm$^{-1}$.

U.V. (EtOH) $\lambda_{max}$365 nm, $\epsilon_{max}$18,400 1 mol$^{-1}$cm$^{-1}$ $\lambda_{max}$235 nm, $\epsilon_{max}$ 2,900 1 mol$^{-1}$cm$^{-1}$.

N.M.R. (CDCl$_3$) $\delta$0.9(3H, m), 1.25(32H, m), 3.1(3H, t), 7.4(2H, m), 8.6(2H, m).

EXAMPLE 4

Synthesis of 2-(4-phenylthiophenyl)-4,6-bis(trichloromethyl)-1,3,5-triazine 4-(Phenylthio)benzonitrile (1.6 g), trichloroacetonitrile (2.2 g) and aluminium tribromide (0.1 g) were placed in a 3-necked flask, and the mixture was saturated with gaseous HCl whilst being maintained at a temperature of from $-10°$ to $0°$ C. for 30 minutes. After standing for 3 days the mixture was heated and poured into methanol (500 ml); the precipitated solids were collected and recrystallised from ethanol—yield 63%.

m.p. 111°–112° C.

I.R. (Nujol) 665, 700, 725, 770, 780, 810, 830, 855, 925, 1015, 1080, 1115, 1190, 1250, 1350, 1400, 1500, 1555, 1595 cm$^{-1}$.

U.V. (EtOH) $\lambda_{max}$358 nm, $\epsilon_{max}$24,400 1 mol$^{-1}$cm$^{-1}$.

N.M.R. (CDCl$_3$) $\delta$7.2(2H, m), 7.4–7.6(5H, m), 8.5(2H, m).

EXAMPLE 5

Synthesis of 2-(4-(4-methoxyphenyl)thiophenyl)-4,6-bis(trichloromethyl)-1,3,5-triazine 4-(4-Methoxyphenylthio)benzonitrile (3 g), trichloroacetonitrile (3.6 g) and aluminium tribromide (0.1 g) were placed in a 3-necked flask, and the mixture was saturated with gaseous HCl whilst being maintained at a temperature of $-10°$ to $0°$ C. for 30 minutes. After standing for 3 days the mixture was heated and poured into methanol (500 ml); the precipitated solids were collected and recrystallised from ethanol—yield 64%.

m.p. 136°–137° C.

I.R. (Nujol) 665, 700, 720, 775, 815, 830, 835, 855, 925, 960, 970, 990, 1015, 1025, 1080, 1100, 1110, 1115, 1175, 1185, 1250, 1290, 1300, 1350, 1360, 1400, 1500, 1555, 1595 cm$^{-1}$.

U.V. (EtOH) $\lambda_{max}$228 nm, $\epsilon_{max}$25,000 1 mol$^{-1}$cm$^{-1}$, $\lambda_{max}$284 nm, $\epsilon_{max}$36,300 1 mol$^{-1}$ cm$^{-1}$, $\lambda_{max}$361 nm, $\epsilon_{max}$ 3,600 1 mol$^{-1}$cm$^{-1}$.

N.M.R. (CDCl$_3$) $\delta$3.8(3H, m), 6.9(2H, m), 7.1(2H, m), 7.5(2H, m), 8.5(2H, m).

EXAMPLE 6

Synthesis of 2-(4-methylthiophenyl)-4,6-bis(tribromomethyl)-1,3,5-triazine 4-(Methylthio)benzonitrile (5 g), tribromoacetonitrile (23 g) and aluminium tribromide (0.7 g) were placed in a 3-necked flask, and the mixture was saturated with gaseous HCl whilst being maintained at a temperature of 15° to 25° C. for 30 minutes. After standing for 3 days, the mixture was heated and poured into methanol (1 liter), the mixture heated and the precipitated solids collected—yield 36%.

m.p. 156°–157° C.

I.R. (Nujol) 620, 660, 695, 740, 815, 1090, 1536, 1590 cm$^{-1}$.

U.V. (EtOH) $\lambda_{max}$235 nm, $\epsilon_{max}$22,900 1 mol$^{-1}$cm$^{-1}$ $\lambda_{max}$355 nm, $\epsilon_{max}$41,100 1 mol$^{-1}$cm$^{-1}$.

N.M.R. (CDCl$_3$) $\delta$8.6(2H, d), 7.4(2H, d) 2.6(3H, s).

EXAMPLE 7

A coating composition was prepared from the following ingredients:

10 ml 20% naphthoquinone diazide/novolak resin in oxitol 2 ml 1% Basonyl Blue in dimethylformamide 2 ml 1% Ethyl Violet in dimethylformamide 5 ml 1% 2-(4-methylthiophenyl)-4,6-bis(trichlomethyl)-1,3,5-triazine in dimethylformamide The composition was coated onto anodised aluminium, dried, exposed for 30 seconds in a 5 kW Montakop exposure unit, and developed with an aqueous alkaline developer.

EXAMPLE 8

A coating composition was prepared from the following ingredients:

16 ml 5% cellulose acetate butyrate in dimethylformamide 8 ml 10% polyester acrylate in dimethylformamide 4 ml 10% dipentaerythritol monohydroxypenta-acrylate in dimethylformamide 10 ml 1% 2-(4-methylthiophenyl)-4,6-bis(trichlomethyl)-1,3,5-triazine in dimethylformamide.

The composition was coated onto anodised aluminium, dried, optionally overcoated with poly(vinyl alcohol), exposed, and developed with an organic solvent developer.

We claim:

1. A triazine derivative of the formula

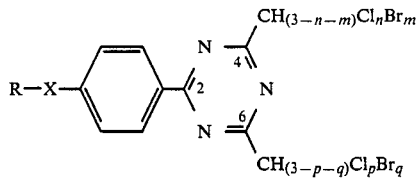

wherein R is selected from the group consisting of an alkyl group containing from 1 to 20 carbon atoms, a phenyl group and a methoxy substituted phenyl group, X is selected from the group consisting of S, Se and Te, n or m is 0, or each is an integer of from 1 to 3, the total sum of n+m not being greater than 3, and p or q is 0, or each is an integer of from 1 to 3, the total sum of p+q not being greater than 3.

2. Compound according to claim 1 wherein the triazine group contains identical substituents at positions 4 and 6 thereof.

3. Compound according to claim 1 wherein n is 3, m is 0, p is 3 and q is 0.

4. Compound according to claim 1 wherein R is an alkyl group containing from 1 to 20 carbon atoms.

5. Compound according to claim 1 which is 2-(4-methylthiophenyl)-4,6-bis(trichloromethyl)-1,3,5-triazine.

6. Compound according to claim 1 which is 2-(4-ethylthiophenyl)-4,6-bis(trichloromethyl)-1,3,5-triazine.

7. Compound according to claim 1 which is 2-(4-stearylthiophenyl)-4,6-bis(trichloromethyl)-1,3,5-triazine.

8. Compound according to claim 1 which is 2-(4-phenylthiophenyl)-4,6-bis(trichloromethyl)-1,3,5-triazine.

9. Compound according to claim 1 which is 2-(4-methylthiophenyl)-4,6-bis(tribromomethyl)-1,3,5-triazine.

* * * * *